(12) United States Patent
Mestha et al.

(10) Patent No.: US 9,521,335 B2
(45) Date of Patent: Dec. 13, 2016

(54) DETECTING FEBRILE SEIZURE WITH A THERMAL VIDEO CAMERA

(71) Applicant: Xerox Corporation, Norwalk, CT (US)

(72) Inventors: Lalit Keshav Mestha, Fairport, NY (US); Beilei Xu, Penfield, NY (US); Rakesh Suresh Kulkarni, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 380 days.

(21) Appl. No.: 14/306,817

(22) Filed: Jun. 17, 2014

(65) Prior Publication Data

US 2015/0363928 A1    Dec. 17, 2015

(51) Int. Cl.

| | |
|---|---|
| *G06K 9/00* | (2006.01) |
| *H04N 5/33* | (2006.01) |
| *G01J 5/10* | (2006.01) |
| *G01J 5/08* | (2006.01) |
| *H04N 5/30* | (2006.01) |
| *A61B 5/01* | (2006.01) |
| *G01J 5/02* | (2006.01) |

(Continued)

(52) U.S. Cl.
CPC ........ *H04N 5/33* (2013.01); *A61B 5/01* (2013.01); *A61B 5/015* (2013.01); *G01J 5/0025* (2013.01); *G01J 5/025* (2013.01); *G01J 5/089* (2013.01); *G01J 5/10* (2013.01); *G06T 7/0016* (2013.01); *H04N 5/30* (2013.01); *A61B 5/0077* (2013.01); *G01J 2005/0077* (2013.01); *G06T 2207/10016* (2013.01); *G06T 2207/10048* (2013.01); *G06T 2207/30076* (2013.01); *G06T 2207/30088* (2013.01)

(58) Field of Classification Search
USPC .. 382/128, 130, 131, 132, 190, 209; 128/922, 923
See application file for complete search history.

(56) References Cited

U.S. PATENT DOCUMENTS 7,209,787 B2 * 4/2007 DiLorenzo ........... A61N 1/3605
                                                    607/45
7,539,533 B2 * 5/2009 Tran ..................... A61B 5/0022
                                                    600/509

(Continued)

OTHER PUBLICATIONS

U.S. Department of Health and Human Services, "Febrile Seizures", NIH Publication No. 12-3930, Sep. 2012.

*Primary Examiner* — Yosef Kassa
(74) *Attorney, Agent, or Firm* — Phillip E. Blair; Fleit Gibbons Gutman Bongini & Bianco P.L.

(57) ABSTRACT

What is disclosed is a system and method for detecting febrile seizure using a thermal video camera. In one embodiment, a video is received comprising time-sequential thermal images of a subject. The video is acquired of the subject in real-time using a thermal video system. Each thermal image comprises a plurality of pixels with an intensity value of each pixel corresponding to a temperature. The thermal images are processed to determine an occurrence of a febrile seizure. The processing involves identifying a region of interest in the thermal image and determining a temperature for the region of interest based on values of the pixels isolated in that region of interest. Thereafter, a rate of change of temperatures is obtained for the subject in real-time on a per-frame basis. If the rate of change is determined to have exceeded a pre-defined threshold level, then the subject is having a febrile seizure.

24 Claims, 5 Drawing Sheets

(51) Int. Cl.
*G06T 7/00* (2006.01)
*G01J 5/00* (2006.01)
*A61B 5/00* (2006.01)

(56) References Cited

U.S. PATENT DOCUMENTS

| | | | | |
|---|---|---|---|---|
| 7,591,793 | B2* | 9/2009 | Orito | A61B 5/1114 |
| | | | | 128/923 |
| 7,643,655 | B2* | 1/2010 | Liang | G06K 9/00335 |
| | | | | 119/421 |
| 7,643,881 | B2* | 1/2010 | Armstrong | A61B 5/01 |
| | | | | 600/549 |
| 8,109,891 | B2* | 2/2012 | Kramer | A61B 5/1118 |
| | | | | 600/595 |
| 8,497,857 | B2* | 7/2013 | Nakamura | G09G 3/3225 |
| | | | | 257/59 |
| 8,520,074 | B2 | 8/2013 | Wang et al. | |
| 8,587,657 | B2 | 11/2013 | Wang et al. | |
| 2013/0147959 | A1 | 6/2013 | Wang et al. | |

* cited by examiner

DETECTING FEBRILE SEIZURE WITH A THERMAL VIDEO CAMERA

TECHNICAL FIELD

The present invention is directed to systems and methods which use a thermal video camera system to determine whether a patient is having a febrile seizure.

BACKGROUND

Many people are susceptible to seizure, depending on the circumstances. A seizure is the uncontrolled electrical activity in the brain, which may produce convulsion, muscle twitch, and confusion, to name a few. The type of symptoms depends on where the abnormal electrical activity is occurring in the patient's brain, what its cause is, and such factors as patient age and overall health. Seizures can be caused by head injury, a brain tumor, heavy metal poisoning, infection, genetics, and fever. Febrile seizures are convulsions brought on by a fever in infants or children. Febrile seizures usually occur between the ages of 6 months and 5 years. Children rarely have their first febrile seizure before the age of 6 months or after 3 years of age. The older a child is when their first febrile seizure occurs, the less likely that the child will have another. During febrile seizure, it is common for the child to lose consciousness and shake. Less commonly, the child becomes rigid or twitches on the right or left side of their body. Some febrile seizure events can be as brief as a few seconds while others may last for more than 10 minutes. Most febrile seizures last only a minute or two.

Approximately 1 in 25 children will have a febrile seizure, many without even being aware that a seizure has occurred. More than ⅓ of this group of children will have multiple febrile seizures. A few factors appear to boost a child's risk of having recurrent febrile seizures, i.e., age (less than 15 months old) at the time of their first febrile seizure event, frequent high fevers, and a family history of febrile seizures. Febrile seizures most often occur during the first day of a child's fever. If the seizure occurs soon after a fever has begun or when the fever temperature is relatively low, the risk of recurrence is higher. Although a febrile seizure can be frightening, the vast majority of febrile seizures are relatively harmless however there is a risk that the child may be injured by falling or by choking if there is food in the mouth at the time of the seizure. There is no evidence that short febrile seizures cause brain damage. Children with febrile seizures have normal academic achievement when compared to children with no history of seizure. Most children recover completely but a few might be at risk of subsequent seizures without fever (epilepsy). Children having febrile seizures are not considered to have epilepsy because epileptic seizures are not triggered by fever. About 95 percent of children who experience febrile seizures do not develop epilepsy. Although the risk of developing epilepsy is quite small, some groups of children having febrile seizures such as those with cerebral palsy or other neurological conditions, have an increased risk of developing epilepsy. Children who have prolonged febrile seizures (i.e., those lasting longer than one hour) or seizures that affect only part of the body, or seizures that recur within 24 hours, are at a higher risk for epilepsy. It is rare that children who do not have any of the risk factors end up developing epilepsy. For more information, the reader is directed to the National Institute of Health (NIH) and, more particularly, to the National Institute of Neurological Disorders and Stroke (NINDS).

Accordingly, what is desired in this art are increasingly sophisticated systems and methods for detecting febrile seizure.

INCORPORATED REFERENCES

The following U.S. Patents, U.S. Patent Applications, and Publications are incorporated herein in their entirety by reference.

"Determining A Total Number Of People In An IR Image Obtained Via An IR Imaging System", U.S. Pat. No. 8,520,074, by Wang et al.

"Determining A Number Of Objects In An IR Image", U.S. Pat. No. 8,587,657, by Wang et al.

"Determining A Pixel Classification Threshold For Vehicle Occupancy Detection", U.S. patent application Ser. No. 13/324,308, by Wang et al.

BRIEF SUMMARY

What is disclosed is a system and method for detecting febrile seizure with a thermal video system. In one embodiment, a video is received comprising time-sequential thermal images of an area of exposed skin of a subject being monitored for the occurrence of a febrile seizure event. Each thermal image comprises a plurality of pixels with an intensity value of each pixel corresponding to a surface temperature. The thermal images are processed to determine an occurrence of a febrile seizure. The processing involves identifying a region of interest in the thermal image and determining a temperature for the region of interest based on values of the pixels isolated in the region of interest. Thereafter, a rate of change of the subject's temperature is determined to ascertain how fast the subject's fever is rising. If the rate of change exceeds a threshold level then the subject is having a febrile seizure.

Features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

Figure 1:
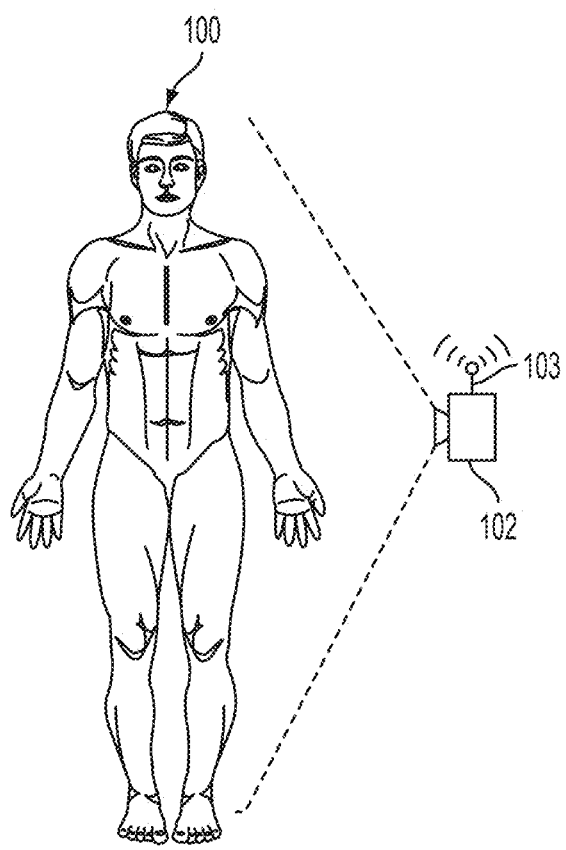
FIG. 1 shows an example subject being imaged by a thermal video system.

What is disclosed is a system and method for detecting febrile seizure with a thermal video system.
Non-Limiting Definitions A "subject" is a living person. FIG. 1 shows a front (anterior) view of a subject 100. Although shown as an adult, the subject of FIG. 1 may be a child. Although the term "person" or "patient" may be used throughout this disclosure, it should be appreciated that the subject may be something other than a human such as, for example, a primate. Therefore, the use of such terms is not to be viewed as limiting the scope of the appended claims strictly to humans. Video of the subject being monitored is captured by a thermal video system.

Figure 2:
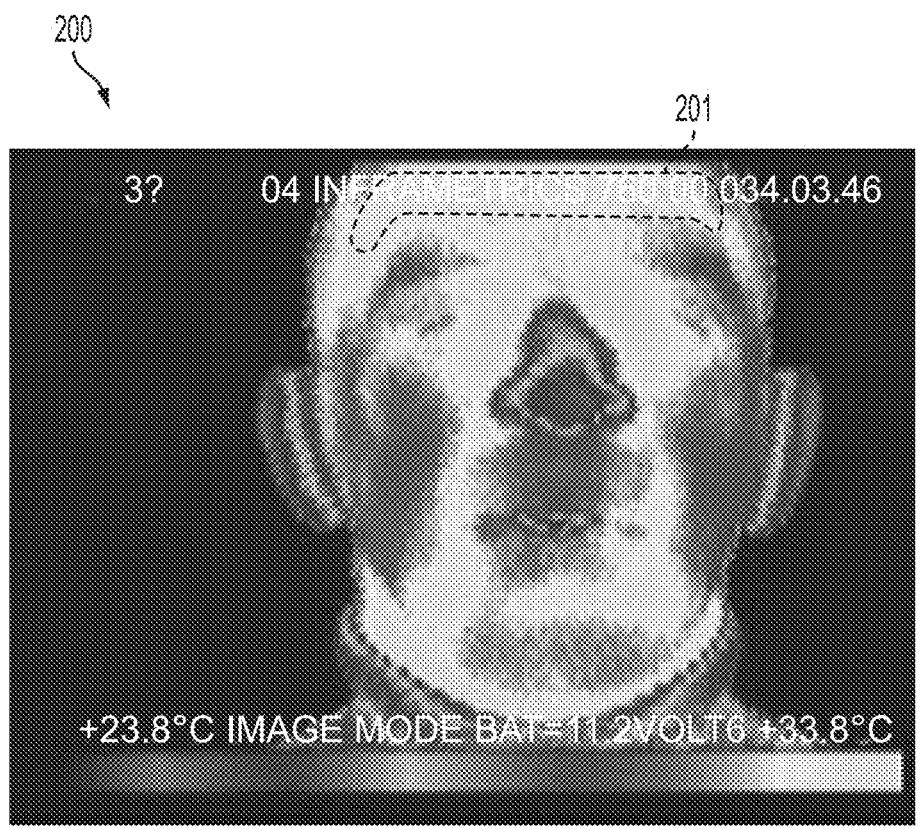
FIG. 2 is a thermal image of the subject of FIG. 1 with a region of interest having been identified in the forehead area.

A "thermal video system" is a video camera with single or multiple spectral bands capable of acquiring video, as is commonly understood, in a desired temperature band. In FIG. 1, an example thermal video system 102 is acquiring video comprising time-sequential thermal image frames of the subject 100. The thermal image frames are communicated to a remote device via a wireless communication element 103, shown as an antenna. Because the amount of black-body radiation emitted by an object increases with the object's temperature, variations in temperature are visible in the thermal image. FIG. 2 shows an example thermal image 200 of the subject in FIG. 1. Thermal video cameras generally consist of optics comprising specialized FPA sensors (focal plane arrays) that respond to defined wavelengths in the electromagnetic spectrum; a detector for detecting radiation in the desired wavelength range; an amplifier circuit; a display; and signal processing hardware for reconstructing the thermal image. Thermal video cameras typically have outputs for retrieving the thermal images. In one embodiment, the thermal video system incorporates a processor executing machine readable program instructions for analyzing thermal images in real-time to effectuate febrile seizure determination in accordance with the methods disclosed herein. Thermal video cameras offer a relatively large dynamic range of temperature settings. For the purposes hereof, it is preferable that the temperature range of the thermal video camera be relatively small and centered around the subject's body surface temperature so that small temperature variations in the skin surface are amplified in terms of pixel color changes to provide a better measure of the subject's temperature. The lens of the thermal video camera is preferably zoomed-in to capture a large number of pixels of skin surface for temperature determination. Thermal video systems such as: a single-band infrared video camera, a multi-band infrared video camera in the thermal range, and a multi-spectral infrared video camera in the thermal range, are available from different vendors in various forms in various streams of commerce. The video captured by the thermal video system is received for processing.

"Receiving a video" is intended to be widely construed and includes: retrieving, receiving, capturing, acquiring, or otherwise obtaining time-sequential thermal images for processing in accordance with the methods disclosed herein. The video can be retrieved from a memory or storage device of the thermal video camera, or obtained from a remote device over a network. The video may be retrieved from a media such as a CDROM or DVD, or downloaded from a web-based system which makes thermal images available for processing. The video can also be retrieved and processed using a smartphone device or using a computing device such as, for example, a laptop, tablet-PC, a workstation, and a remote device over a network. Thermal image frames of the video are processed to identify one or more regions of interest.

A "region of interest" is an area of exposed skin of the subject as seen through the lens of the thermal video camera. FIG. 2 show an example region of interest 201 in the forehead area of the subject. It should be appreciated that other regions of interest can be identified and that the scope of the appended claims should not be viewed as being strictly limited solely to the face. A region of interest can be any location on the subject's body where the medical profession decides the subject's temperature is to be obtained. Pixels in a region of interest are isolated for processing.

"Isolating pixels in a region of interest" can be effectuated using techniques which include: pixel classification, color, texture, spatial features, spectral information, facial recognition, object identification, pattern recognition, and a user input. Methods for classifying pixels are disclosed in several of the above-incorporated references by Wang et al. Pixels may be weighted, averaged, or normalized, or discarded. Isolated pixels are processed to determine a temperature for the subject on a per-frame basis.

"Determining a temperature for the subject" means to analyze the values associated with the isolated pixels to obtain a temperature value for the subject on a frame-by-frame basis. This can be effectuated by integrating pixel values over at least a portion of the region(s) of interest, or by weighted averaging pixel values over at least a portion of the region(s) of interest. Based on temperature values determined for the subject on a per-frame basis, a rate of temperature change is identified in real-time.

A "rate of change of temperature" is a measure of how fast the subject's fever is rising. The rate of change is compared to a threshold.

A "threshold level" is used to determine whether the subject's temperature is changing rapidly at a rate to be indicative of a febrile seizure event or is holding relatively constant. The threshold level will vary from patient to patient and is therefore set by the medical professional based on the subject's age, physical condition, overall health and vitals. Therefore, a discussion as to a specific threshold level has been omitted herein. The threshold can based on historical data which includes rates of fever progressions of patients who have had febrile seizures. A user, technician, or medical professional may use a mouse or a touchscreen display, for example, to pre-set or otherwise select the threshold. The threshold may be dynamically adjusted during video acquisition. The subject's health vitals may further be used to facilitate the determination of a febrile seizure event. Health vitals include: cardiac pulse rate, blood pressure, respiration rate, evidence of muscle twitch, and signals from electrocardiogram (ECG/EKG) and electroencephalogram (EEG) devices. In one embodiment, a threshold level is also set for movement to determine whether the movement is excessive.

A "threshold for movement" is used during video acquisition of the subject to determine whether movement occurred that is sufficient to introduce motion artifacts into the video which will impact temperature determination. The threshold for movement can be based on a type of motion or the source of motion (i.e., by the subject or by the environment). The threshold for movement may be pre-set, manually adjusted, or automatically adjusted in real-time. Movement can be determined in real-time by, for instance, analyzing pixels in the thermal images, facial recognition, object tracking, using a motion detector, or by visually observing the subject. The threshold for movement will largely depend on the application where the teachings hereof find their intended uses. Therefore, a discussion with respect to a particular threshold for movement is omitted. In one embodiment, if the movement is determined to be above the threshold set for movement then the thermal images acquired during the time interval when the movement occurred are ignored or otherwise discarded. In other embodiments, responses to movement exceeding the threshold include: adjusting a position of the thermal video camera; adjusting a position of the subject; changing a frame rate of the thermal video camera; swapping the thermal video camera for another thermal video camera; signaling that movement has occurred; or stopping video acquisition altogether.

"Initiating a notification" means to communicate any of: an audio message, a text message, an email, a voicemail message, a phone call, a video, and an image. The notification may comprise an alert signal such as a bell or an alarm, or a visual notification such as a blinking light, or the like. The notification can be initiated automatically or manually.

"Processing broadly includes the application of any mathematical operation applied to data, according to any specific context, or for any specific purpose.

Example Flow Diagram

Figure 3:
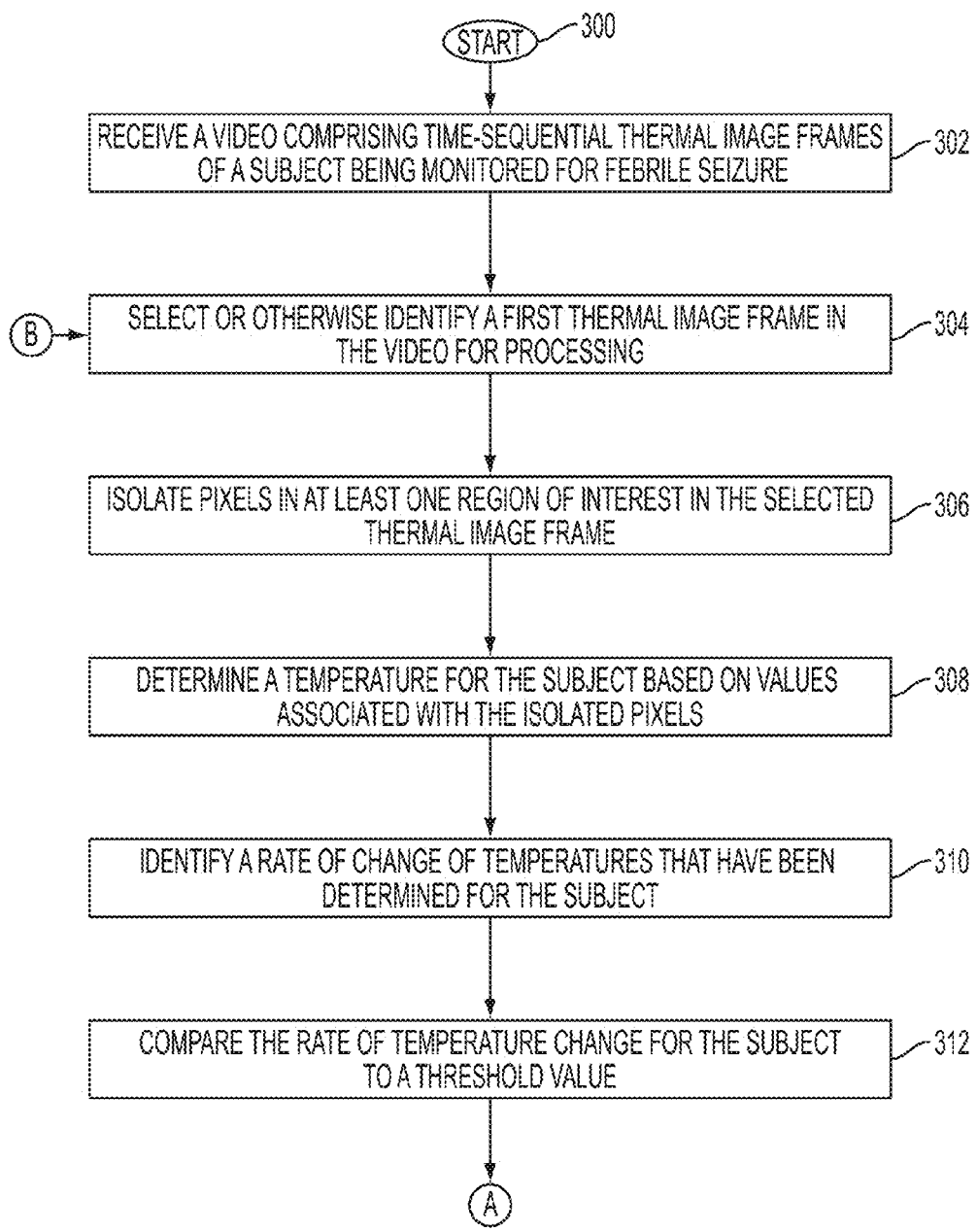
FIG. 3 is a flow diagram which illustrates one example embodiment of the present method for detecting a febrile seizure for a subject using a thermal video system.

Reference is now being made to the flow diagram of FIG. 3 which illustrates one example embodiment of the present method for detecting a febrile seizure for a subject using a thermal video system. Flow processing begins at step 300 and immediately proceeds to step 302.

At step 302, receive a video comprising time-sequential frames of thermal images of a subject being monitored for febrile seizure. The video is being actively acquired by a thermal video system. Each thermal image comprises a plurality of pixels. An intensity value of each pixel corresponds to a surface temperature.

At step 304, select a first thermal image frame in the video for processing. Thermal image frames can be selected or otherwise identified for processing automatically as they are received. The thermal image frames may be processed in batches, depending on the implementation. It should be appreciated that the present method is used to detect the occurrence of a febrile seizure event for the subject in the video in a real-time setting. Thus, it is preferable that the thermal image frames of the video are processed as they are being acquired by the thermal video system being utilized. Previously acquired video of the subject can be processed off-line to refine the algorithms used for real-time processing or for explanatory purposes.

At step 306, isolate pixels in at least one region of interest in the selected thermal image frame. One example region of interest is shown in the thermal image of FIG. 2.

At step 308, determine a temperature for the subject based on values associated with the isolated pixels. In various embodiments, this is effectuated by integrating pixel values over at least a portion of the region of interest or by weighted averaging pixel values over at least a portion of the region of interest.

At step 310, identify a rate of change of temperatures that have been determined for the subject. This is done to obtain a temperature gradient with respect to time to see how fast the subject's fever is progressing. On a first iteration, the subject's temperature is stored to a memory or storage device for subsequent retrieval.

At step 312, compare the rate of change to a threshold. The threshold is preferably set by a medical professional based on historical records of patients who have had one or more febrile seizures.

Figure 4:
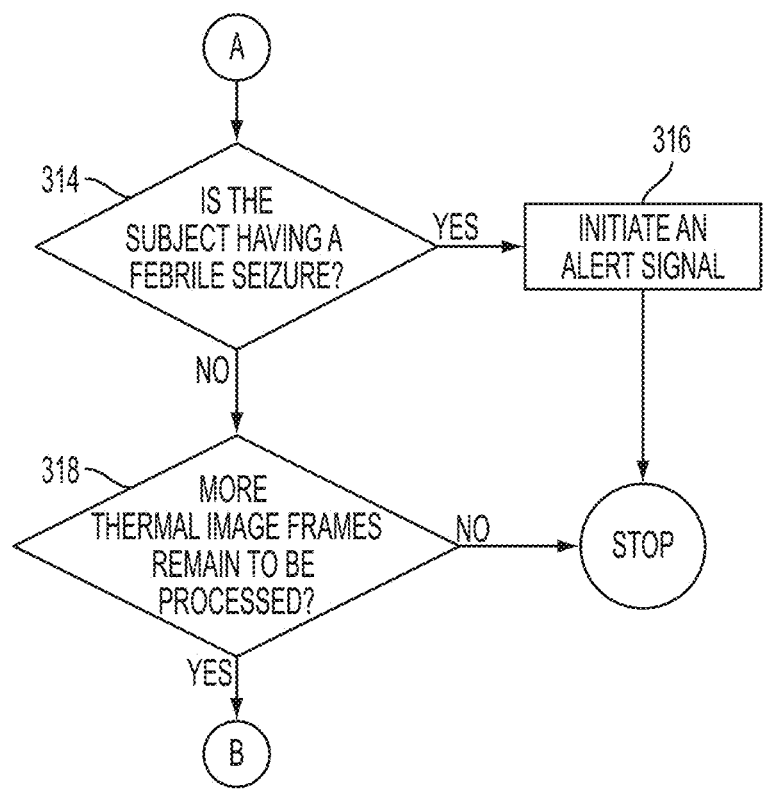
FIG. 4 is a continuation of the flow diagram of FIG. 3 with flow processing continuing with respect to node A.

Reference is now being made to the flow diagram of FIG. 4 which is a continuation of the flow diagram of FIG. 3 with flow processing continuing with respect to node A.

At step 314, a determination is made whether, as a result of the comparison (of step 312), that the subject is having a febrile seizure. If the subject is having a febrile seizure then, at step 316, an alert signal is initiated. The alert may take the form of a message displayed on a display device or a sound activated at, for example, a nurse's station or a display of a device. The alert may take the form of a colored or blinking light which provides a visible indication that a seizure event is occurring. The alert can be a notification such as a text, audio, and/or video message. The alert may be communicated to one or more remote devices over a wired or wireless network. The alert may be sent directly to a wireless cellular device of a parent, guardian, or medical professional. Additional actions would be taken in response to the alert. In this embodiment, after the alert signal is initiated, further processing stops. Otherwise, processing continues with respect to step 318.

At step 318, a determination is made whether more thermal image frames remain to be processed. If so then processing continues with respect to node B wherein, at step 304, a next thermal image frame in the received video is selected for processing. Pixels are isolated in the one or more regions of interest in the next thermal image frame and a temperature is determined for the subject based on values associated with the isolated pixels. The rate of change is again determined and compared to the threshold level. Thereafter, another determination is made whether the subject is having a febrile seizure. Processing continuously repeats in a similar manner until no more thermal image frames remain to be processed. It should be understood that the methods hereof are preferably used for real-time patient monitoring in an environment wherein video is being continuously acquired of the subject by the thermal video camera and processed on a continuous basis until video acquisition is terminated.

The flow diagrams depicted herein are illustrative. One or more of the operations may be performed in a differing order. Other operations may be added, modified, enhanced, or consolidated. Variations thereof are intended to fall within the scope of the appended claims.

Example Wireless Networked System

Figure 5:
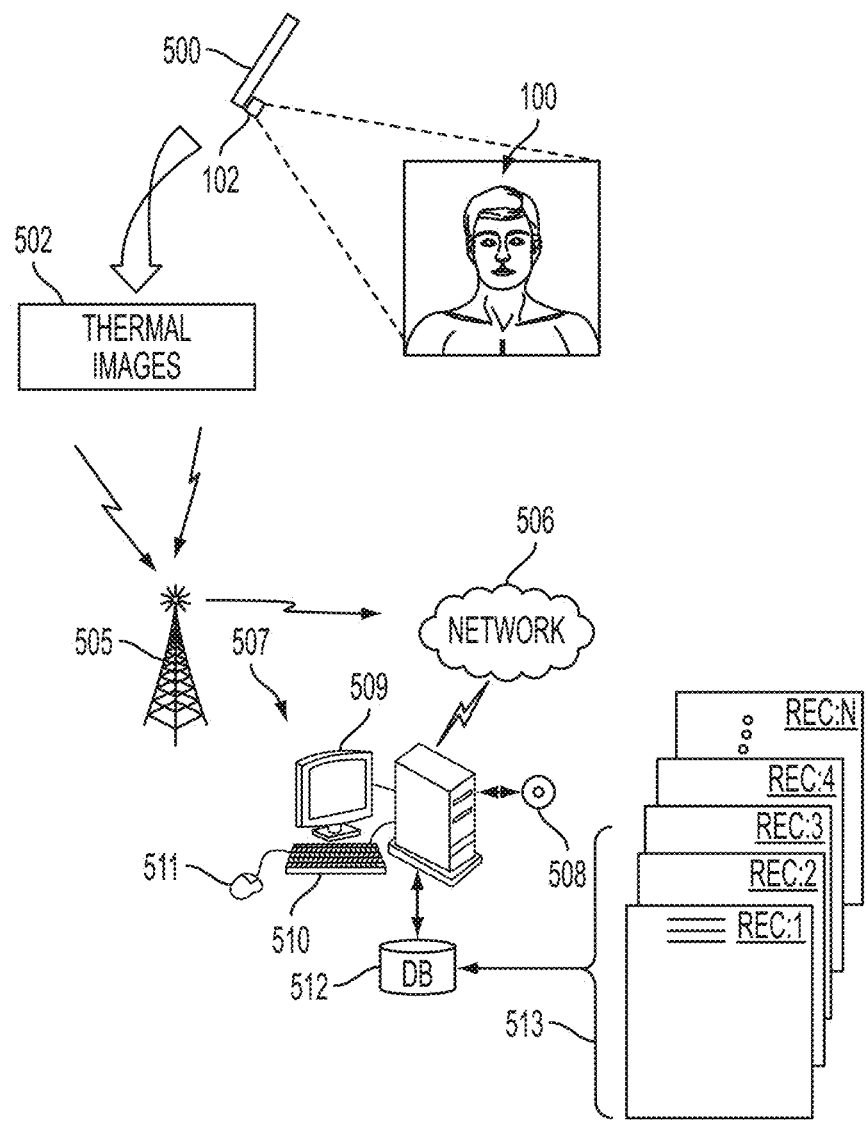
FIG. 5 is a block diagram of one example system for performing various aspects of the present method as described with respect to the flow diagrams of FIGS. 3-4.

Reference is now being made to FIG. 5 which shows a block diagram of one example system for performing various aspects of the present method as described with respect to the flow diagrams of FIGS. 3-4. The embodiment shown is illustrative and should not be viewed as limiting the scope of the appended claims strictly to this configuration.

In FIG. 5, handheld smartphone device 500 is shown using an integrated thermal video camera 102 to capture thermal images of a patient 100. The smartphone incorporates non-volatile memory and internal storage for storing variables, formulas, tables, results, applications, software tools, and the like. Any of these may be stored/retrieved from internal storage or non-volatile memory as needed. Further, the smartphone is functionally enabled to send/receive email, text, audio, video, a phone call, an alert, and communicate with a remote device via a wireless cellular connection. The device has a tactile function induced by activating an oscillating cam that introduces a vibration sensation into the chassis of the handheld device. Global Positioning System (GPS) capability is also enabled. Some handheld devices have a slideably retractable keyboard in lieu of, or in addition to, a virtual keyboard. Thermal images 502 capture by the thermal video camera of the smartphone 500 are wirelessly communicated to a cellular communication tower 505 which transmits the thermal image frames to a server (not shown) on a network 506.

A remote computing device, shown as a workstation 507, is communicatively coupled to the network via wired or wireless pathways. Such a workstation may be in a nurse's station or in a remote location some distance away from the location of the patient 100. The workstation has a computer case which houses various components such as a motherboard with a processor and memory, a network card, a video card, a hard drive capable of reading/writing to machine readable media 508 such as a floppy disk, optical disk, CD-ROM, DVD, magnetic tape, and the like, and other software and hardware needed to perform the functionality of a workstation, as is widely understood. A hard drive, internal to the computer case, stores mathematical formulae, functions, and the like, as need for performing region of interest identification, pixel isolation, temperature determination, threshold comparison, and the like, as disclosed herein.

The workstation further includes a display device 509, such as a CRT, LCD, or touchscreen device Thermal images, temperature values, rates of change, threshold levels, including other patient vitals such as heart rate, respiration rate, blood pressure, to name a few, can be displayed on the display screen 509. A medical professional can use the display to monitor the patient before, during or after the occurrence of a febrile seizure. Values, algorithms, variables, results of interim calculations, and the like, performed by the workstation can also be displayed. A user or technician can view any of the received information and make selections from displayed menu options. Keyboard 510 and mouse 511 effectuate a user input or selection.

Database 512 contains records (collectively at 513). Records stored in the database can be manipulated, updated, and retrieved in response to a query. Information stored on these records takes the form of patient medical histories associated with episodes of febrile seizures, temperature values, thermal images, to name a few. Such records may also include information identifying patients, diagnoses, prognoses, and treatments. Although the database is shown as an external unit of hardware, the database may be internal to the workstation mounted, for example, on a hard disk housed in the computer case.

It should be appreciated that the workstation has an operating system and other specialized software configured to display alphanumeric values, menus, scroll bars, dials, slideable bars, pull-down options, selectable buttons, and the like, for entering, selecting, modifying, and accepting information needed for processing the thermal image frames in accordance with the methods disclosed herein, and for enabling a medical practitioner to make a preliminary diagnosis of febrile seizure. The user interface of the workstation can be utilized to set parameters, select images or portions thereof for processing, identify one or more regions of interest, set threshold levels, adjust camera settings, etc. These selections, including the received video image frames and other signals, may be stored to storage devices 508 and 512. Default settings and initial values and other parameters can be retrieved from either the storage devices, as needed. A practitioner may further communicate instructions back to the user via the handheld device, depending on the implementation, to instruct them, for instance to take steps, perform actions, or acquire video of the subject from a different perspective or to zoom-in on a particular region of the subject's body.

Results may be communicated to other practitioners for their review and input over the wireless network 506 and/or the cell tower 505. The received video can be communicated to other professionals, secondary or tertiary service providers and government agencies, depending on the implementation. Various aggregate summaries can be computed using patient data. These include, but are not limited to: longitudinal analyses involving statistics of patient cases; population-based studies of patients within one or more subpopulations; geography-based studies involving patients in specified geographical areas; and socio-economic and community-based studies involving patients in a specified social or economic community. Further, by combining knowledge of genetics, more sophisticated modeling and analyses can also be performed to assess febrile seizures from a genetic standpoint.

It should be appreciated that some or all of the functionality performed by the workstation may be performed, in whole or in part, by the smartphone which, alternatively, may be a laptop or tablet-PC. Although shown as a workstation, it can be: an ASIC, tablet, notebook, laptop, server, or mainframe. The embodiment of the workstation is illustrative and may include other functionality known in the arts.

The teachings hereof can be implemented in hardware or software using any known or later developed systems, structures, devices, and/or software by those skilled in the applicable art without undue experimentation from the functional description provided herein with a general knowledge of the relevant arts. One or more aspects of the methods described herein are intended to be incorporated in an article of manufacture. The article of manufacture may be shipped, sold, leased, or otherwise provided separately either alone or as part of a product suite or a service.

The above-disclosed and other features and functions, or alternatives thereof, may be desirably combined into other different systems or applications. Presently unforeseen or unanticipated alternatives, modifications, variations, or improvements may become apparent and/or subsequently made by those skilled in this art which are also intended to be encompassed by the following claims. The teachings of any publications referenced herein are hereby incorporated by reference in their entirety.

What is claimed is:

1. A method for detecting febrile seizure using a thermal video device, the method comprising:
   receiving a video comprising time-sequential frames of thermal images of a subject being monitored for febrile seizure, said video being acquired by a thermal video system, each thermal image comprising a plurality of pixels, an intensity value of each pixel corresponding to a surface temperature; and
   processing thermal images to determine an occurrence of a febrile seizure, said processing comprising:
      isolating pixels associated with at least one region of interest;
      determining a temperature for the subject based on values of said pixels isolated in said region of interest;
      determining a rate of change of said subject's temperature; and
      in response to said rate of change exceeding a threshold level, determining that said subject is having a febrile seizure.

2. The method of claim 1, wherein said thermal video system is any of: a single-band infrared video camera, a multi-band infrared video camera in the thermal range, and a multi-spectral infrared video camera in the thermal range.

3. The method of claim 1, wherein pixels are isolated in the regions of interest using any of: pixel classification, color, texture, spatial features, spectral information, facial recognition, object identification, pattern recognition, and a user input.

4. The method of claim 1, wherein determining a temperature for said subject comprises any of:
  integrating pixel values over at least a portion of said region of interest; and
  weighted averaging pixel values over at least a portion of said region of interest.

5. The method of claim 1, further comprising:
  weighting values of any of said isolated pixels;
  averaging values of any of said isolated pixels;
  normalizing values of any of said isolated pixels; and
  discarding any pixels with intensity values below a level of acceptability.

6. The method of claim 1, wherein said threshold is based on any of:
  a rate of fever progression of patients who have had a febrile seizure; and
  a user input.

7. The method of claim 1, wherein said determination of febrile seizure further utilizes health vitals of said subject comprising any of: cardiac pulse rate, blood pressure, respiration rate, muscle twitch, a signal from an electrocardiogram (ECG/EKG), and a signal from electroencephalogram (EEG).

8. The method of claim 1, further comprising determining whether a movement occurred during video acquisition which is likely to adversely impact said temperature determination, comprising any of:
  analyzing pixels in said thermal image;
  performing facial recognition on said thermal image;
  performing object tracking on said thermal image;
  performing pattern recognition on said thermal image;
  using a motion detector; and
  visually observing said subject.

9. The method of claim 8, wherein, in response to said determination, further comprising any of:
  adjusting a position of said thermal video system;
  adjusting a position of said subject;
  changing a frame rate of said thermal video system;
  swapping said thermal video system for another thermal video system;
  ignoring video image frames captured during movement;
  initiating an alert that movement has occurred; and
  stopping video acquisition altogether.

10. The method of claim 1, further comprising communicating said rate of change to any of: a display device, a storage device, a smartphone, a laptop, tablet-PC, a workstation, and a remote device over a network.

11. The method of claim 1, wherein, in response to said subject having a febrile seizure, initiating a notification comprising any of: an audio message, a text message, an email, a voicemail message, a phone call, a video, an image, and an alert signal.

12. The method of claim 1, wherein said video is a streaming video and febrile seizure determination occurs in real-time.

13. A thermal video system for detecting febrile seizure using a thermal video device, the system comprising:
  a video camera a video comprising time-sequential frames of thermal images, each thermal image comprising a plurality of pixels, an intensity value of each pixel corresponding to a surface temperature; and
  a processor in communication with a memory, said processor executing machine readable instructions for performing:
    receiving thermal images of a subject being monitored for febrile seizure;
    isolating pixels associated with at least one region of interest;
    determining a temperature for said subject based on values associated with said isolated pixels;
    determining a rate of change of said subject's temperature; and
    in response to said rate of change exceeding a threshold, determining that said subject is having a febrile seizure.

14. The system of claim 13, wherein said thermal video system is any of: a single-band infrared video camera, a multi-band infrared video camera in the thermal range, and a multi-spectral infrared video camera in the thermal range.

15. The system of claim 13, wherein pixels are isolated in the regions of interest using any of: pixel classification, color, texture, spatial features, spectral information, facial recognition, object identification, pattern recognition, and a user input.

16. The system of claim 13, wherein determining a temperature for said subject comprises any of:
  integrating pixel values over at least a portion of said region of interest; and
  weighted averaging pixel values over at least a portion of said region of interest.

17. The system of claim 13, further comprising:
  weighting values of any of said isolated pixels;
  averaging values of any of said isolated pixels;
  normalizing values of any of said isolated pixels; and
  discarding any pixels with intensity values below a level of acceptability.

18. The system of claim 13, wherein said threshold is based on any of:
  a rate of fever progression of patients who have had a febrile seizure; and
  a user input.

19. The system of claim 13, wherein said determination of febrile seizure further utilizes health vitals of said subject comprising any of: cardiac pulse rate, blood pressure, respiration rate, muscle twitch, a signal from an electrocardiogram (ECG/EKG), and a signal from an electroencephalogram (EEG).

20. The system of claim 13, further comprising determining whether a movement occurred during video acquisition which is likely to adversely impact said temperature determination, comprising any of:
  analyzing pixels in said thermal image;
  performing facial recognition on said thermal image;
  performing object tracking on said thermal image;
  performing pattern recognition on said thermal image;
  using a motion detector; and
  visually observing said subject.

21. The system of claim 20, wherein, in response to said determination, further comprising any of:
  adjusting a position of said thermal video system;
  adjusting a position of said subject;
  changing a frame rate of said thermal video system;
  swapping said thermal video system for another thermal video system;
  ignoring video image frames captured during movement;
  initiating an alert that movement has occurred; and
  stopping video acquisition altogether.

22. The system of claim 13, further comprising communicating said rate of change to any of: a display device, a storage device, a smartphone, a laptop, tablet-PC, a workstation, and a remote device over a network.

23. The system of claim 13, wherein, in response to said subject having a febrile seizure, initiating a notification comprising any of: an audio message, a text message, an email, a voicemail message, a phone call, a video, an image, and an alert signal.

24. The system of claim 13, wherein said video is a streaming video and febrile seizure determination occurs in real-time.

\* \* \* \* \*